US012670582B2

(12) United States Patent
Endo

(10) Patent No.: US 12,670,582 B2
(45) Date of Patent: Jun. 30, 2026

(54) IMAGE PROCESSING APPARATUS, METHOD FOR OPERATING IMAGE PROCESSING APPARATUS, AND ENDOSCOPE SYSTEM FOR INDICATING AN IMAGED AREA AND A NOT-YET-IMAGED AREA OF AN IMAGE

(71) Applicant: FUJIFILM Corporation, Tokyo (JP)

(72) Inventor: Maiko Endo, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 476 days.

(21) Appl. No.: 17/809,218

(22) Filed: Jun. 27, 2022

(65) Prior Publication Data

US 2022/0327702 A1     Oct. 13, 2022

Related U.S. Application Data

(63) Continuation of application No. PCT/JP2021/000820, filed on Jan. 13, 2021.

(30) Foreign Application Priority Data

Jan. 20, 2020    (JP) ................................. 2020-006928

(51) Int. Cl.
*G01T 7/00* (2006.01)
*A61B 1/00* (2006.01)
(Continued)

(52) U.S. Cl.
CPC ........ *G06T 7/0012* (2013.01); *A61B 1/00009* (2013.01); *A61B 1/00045* (2013.01);
(Continued)

(58) Field of Classification Search
CPC ......... G06T 7/0012; G06T 2207/10068; A61B 1/00009; A61B 1/00045; A61B 1/045;
(Continued)

(56) References Cited

U.S. PATENT DOCUMENTS

2009/0185762 A1* 7/2009 He .......................... G06F 16/51
382/305
2013/0304446 A1* 11/2013 Rabinovitz ........ A61B 1/00158
703/11
(Continued)

FOREIGN PATENT DOCUMENTS

CN         108135453 A       6/2018
EP         3 811 845 A1      4/2021
(Continued)

OTHER PUBLICATIONS

International Search Report issued in PCT/JP2021/000820; mailed Apr. 6, 2021.
(Continued)

*Primary Examiner* — Hwa Andrew Lee
(74) *Attorney, Agent, or Firm* — Studebaker Brackett PLLC

(57) ABSTRACT

The present invention enables to report insufficient observation at an appropriate timing. A medical image processing apparatus according to an aspect of the present invention is a medical image processing apparatus including a memory that stores area information indicating predetermined areas to be imaged in a photographic subject, a processor, and a reporting unit. The processor is configured to acquire a medical image of the photographic subject, perform recognition of an area of the photographic subject in the medical image, compare the recognized area with an area indicated by the area information and make a determination of a not-yet-imaged area among the areas to be imaged, and perform, using the reporting unit, reporting of a result of the determination at an expected end timing at which acquisition of the medical image of the areas to be imaged is expected to have been ended.

18 Claims, 13 Drawing Sheets

(51) Int. Cl.

| | | |
|---|---|---|
| *A61B 1/045* | (2006.01) | |
| *G06T 7/00* | (2017.01) | |
| *G16H 30/20* | (2018.01) | |
| *G16H 30/40* | (2018.01) | |

(52) U.S. Cl.
CPC ............. *A61B 1/045* (2013.01); *G16H 30/20* (2018.01); *G16H 30/40* (2018.01); *G06T 2207/10068* (2013.01)

(58) Field of Classification Search
CPC .. A61B 1/0005; A61B 1/00055; G16H 30/20; G16H 30/40; G16H 40/63
See application file for complete search history.

(56) References Cited

U.S. PATENT DOCUMENTS

| | | | |
|---|---|---|---|
| 2016/0000307 A1 | 1/2016 | Akimoto et al. | |
| 2016/0073927 A1 | 3/2016 | Akimoto et al. | |
| 2018/0084970 A1 | 3/2018 | Harada et al. | |
| 2018/0214006 A1* | 8/2018 | Akimoto | A61B 1/00194 |
| 2019/0380617 A1 | 12/2019 | Oosake et al. | |
| 2020/0069160 A1 | 3/2020 | Oosake | |
| 2020/0279368 A1 | 9/2020 | Tada et al. | |
| 2020/0294227 A1 | 9/2020 | Usuda | |
| 2021/0233648 A1 | 7/2021 | Kamon | |
| 2023/0025827 A1* | 1/2023 | Shelton, IV | G16H 40/20 |

FOREIGN PATENT DOCUMENTS

| | | |
|---|---|---|
| EP | 4 082 421 A1 | 11/2022 |
| EP | 4 091 532 A1 | 11/2022 |
| JP | 2012-070936 A | 4/2012 |
| JP | 2016-002206 A | 1/2016 |
| JP | 2016-062488 A | 4/2016 |
| JP | 2018-050890 A | 4/2018 |
| JP | 2018-139847 A | 9/2018 |
| JP | 2018-139848 A | 9/2018 |
| JP | 2020-146202 A | 9/2020 |
| WO | 2014/168128 A1 | 10/2014 |
| WO | 2018/159461 A1 | 9/2018 |
| WO | 2018/221033 A1 | 12/2018 |
| WO | 2018/225448 A1 | 12/2018 |
| WO | 2019/245009 A1 | 12/2019 |
| WO | 2020/090729 A1 | 5/2020 |

OTHER PUBLICATIONS

International Preliminary Report on Patentability (Chapter II) issued in PCT/JP2021/000820; completed Dec. 1, 2021.

An Office Action mailed by the Japan Patent Office on Dec. 11, 2023, which corresponds to Japanese Patent Application No. 2021-573084, and is related to U.S. Appl. No. 17/809,218; with English translation.

An Office Action mailed by the Japan Patent Office on Jun. 4, 2024, which corresponds to Japanese Patent Application No. 2021-573084, and is related to U.S. Appl. No. 17/809,218; with English translation.

The extended European search report issued by the European Patent Office on Jun. 9, 2023, which corresponds to European Patent Application No. 21744902.4-1126 and is related to U.S. Appl. No. 17/809,218.

Communication pursuant to Article 94(3) EPC issued by the European Patent Office on Aug. 22, 2025, which corresponds to European Patent Application No. 21744902.4-1122 and is related to U.S. Appl. No. 17/809,218.

An Office Action mailed by China National Intellectual Property Administration on Apr. 10, 2025, which corresponds to Chinese Patent Application No. 202180009009.7 and is related to U.S. Appl. No. 17/809,218; with English language translation.

An Office Action mailed by China National Intellectual Property Administration on Nov. 18, 2024, which corresponds to Chinese Patent Application No. 202180009009.7 and is related to U.S. Appl. No. 17/809,218; with English language translation.

* cited by examiner

207

700

810

812

802

810

800

814

802

810

800

816

810

802

818

IMAGE PROCESSING APPARATUS, METHOD FOR OPERATING IMAGE PROCESSING APPARATUS, AND ENDOSCOPE SYSTEM FOR INDICATING AN IMAGED AREA AND A NOT-YET-IMAGED AREA OF AN IMAGE

CROSS-REFERENCE TO RELATED APPLICATIONS

The present application is a Continuation of PCT International Application No. PCT/JP2021/000820 filed on Jan. 13, 2021 claiming priority under 35 U.S.C § 119(a) to Japanese Patent Application No. 2020-006928 filed on Jan. 20, 2020. Each of the above applications is hereby expressly incorporated by reference, in its entirety, into the present application.

BACKGROUND OF THE INVENTION

1. Field of the Invention

The present invention relates to a medical image processing apparatus, a method for operating the medical image processing apparatus, and an endoscope system.

2. Description of the Related Art

In an image display apparatus described in JP2018-50890A, a landmark image including an anatomical landmark is detected in an endoscopic image. Furthermore, mapping is performed in which a landmark image is allocated to a landmark portion of a virtual model corresponding to an imaging-target organ, and a plurality of endoscopic images are allocated to corresponding portions of the virtual model by using mutual connection relationships. On the basis of the virtual model in which the plurality of endoscopic images are allocated to the respective portions, a map image depicting an already-imaged region and a not-yet-imaged region of the imaging-target organ is generated, and the map image is displayed on a monitor.

SUMMARY OF THE INVENTION

In screening endoscopy for diagnosing whether a lesion is present or absent, particularly in esophagogastroduodenoscopy, the number of areas to be observed is large and a manipulation skill is required. This involves an issue that insufficient observation may occur if a user (doctor) is inexperienced in endoscopic diagnosis. A method of "using a technique of automatically determining an observed area to prevent observation from being forgotten" may be used to address the foregoing issue. However, there is an issue that constant reporting of an observed area disturbs diagnosis. However, the related art as described in JP2018-50890A does not report a result of evaluation of insufficient imaging at an appropriate timing although the evaluation is performed.

The present invention has been made in view of these circumstances, and an object of the present invention is to provide a medical image processing apparatus, a method for operating the medical image processing apparatus, and an endoscope system that are capable of reporting insufficient observation at an appropriate timing.

A medical image processing apparatus according to a first aspect of the present invention is a medical image processing apparatus including a memory that stores area information indicating a plurality of predetermined areas to be imaged in a photographic subject, a processor, and a reporting unit. The processor is configured to acquire a medical image of the photographic subject, perform recognition of an area of the photographic subject in the medical image, compare the recognized area with an area indicated by the area information and make a determination of a not-yet-imaged area among the plurality of areas to be imaged, and perform, using the reporting unit, reporting of a result of the determination at an expected end timing at which acquisition of the medical image of the plurality of areas to be imaged is expected to have been ended.

In a medical image processing apparatus according to a second aspect, in the first aspect, the processor is configured to accept a user operation indicating the end, and perform reporting of the result of the determination at the expected end timing which is a timing at which the operation is accepted.

In a medical image processing apparatus according to a third aspect, in the first or second aspect, the processor is configured to perform reporting of the result of the determination at the expected end timing which is a timing at which an area to be observed (observation target) is changed from one organ to another organ in a result of the recognition.

In a medical image processing apparatus according to a fourth aspect, in any one of the first to third aspects, the processor is configured to perform reporting of the result of the determination at the expected end timing which is a timing at which a medical image of the photographic subject in a predetermined area is acquired.

In a medical image processing apparatus according to a fifth aspect, in the fourth aspect, the predetermined area is an esophagogastric junction.

In a medical image processing apparatus according to a sixth aspect, in the fourth aspect, the predetermined area is a pharynx.

In a medical image processing apparatus according to a seventh aspect, in any one of the fourth to sixth aspects, the processor is configured to make the determination at a timing at which the medical image of the predetermined area is acquired.

In a medical image processing apparatus according to an eighth aspect, in any one of the first to seventh aspects, the processor is configured to reduce a reporting intensity of the reporting upon elapse of a predesignated time after starting the reporting.

In a medical image processing apparatus according to a ninth aspect, in the first to eighth aspects, the reporting unit includes a display configured to perform screen display of information and/or a speaker configured to output a sound.

In a medical image processing apparatus according to a tenth aspect, in the ninth aspect, the processor is configured to perform the reporting by changing a display mode of the information that is already being screen-displayed on the display and/or an output mode of the sound that is already being output from the speaker.

In a medical image processing apparatus according to an eleventh aspect, in the ninth or tenth aspect, the processor is configured to perform the reporting by causing the display to newly perform screen display of information that is not screen-displayed before the reporting is performed, and/or causing the speaker to newly output a sound that is not output before the reporting starts.

In a medical image processing apparatus according to a twelfth aspect, in any one of the ninth to eleventh aspects, the processor is configured to increase or decrease a reporting intensity of the screen display by the display.

In a medical image processing apparatus according to a thirteenth aspect, in any one of the first to twelfth aspects, the processor is configured to determine that the area has been recognized, in response to at least one of a condition that the photographic subject is continuously in the medical image for a determined time or more, a condition that the photographic subject is in a determined region of the medical image, or a condition that the photographic subject has a determined in-focus degree or more in the medical image being satisfied.

A method for operating a medical image processing apparatus according to a fourteenth aspect of the present invention is a method for operating a medical image processing apparatus including a memory that stores area information indicating a plurality of predetermined areas to be imaged in a photographic subject, a processor, and a reporting unit. The processor is configured to execute an image acquisition step of acquiring a medical image of the photographic subject, an area recognition step of performing recognition of an area of the photographic subject in the medical image, a determination step of comparing the recognized area with an area indicated by the area information and making a determination of a not-yet-imaged area among the plurality of areas to be imaged, and a reporting step of performing, using the reporting unit, reporting of a result of the determination at an expected end timing at which acquisition of the medical image of the plurality of areas to be imaged is expected to have been ended.

The operation method according to the fourteenth aspect may further include configurations similar to those of the second to the thirteenth aspects. In addition, a program that causes a computer to execute the operation method according to the present invention, and a non-transitory recording medium storing a computer-readable code of the program may be included in an aspect of the present invention.

An endoscope system according to a fifteenth aspect of the present invention includes the medical image processing apparatus according to any one of the first to thirteenth aspects, and an endoscope configured to be inserted into a subject as the photographic subject and capture the medical image. The processor is configured to acquire the medical image captured by the endoscope.

In an endoscope system according to a sixteenth aspect, in the fifteenth aspect, the processor is configured to estimate a movement direction of the endoscope, and cause a result of the determination to be reported at the expected end timing which is a timing at which the estimated movement direction is changed to a backward direction.

DESCRIPTION OF THE PREFERRED EMBODIMENTS

Hereinafter, an embodiment of a medical image processing apparatus, a method for operating the medical image processing apparatus, and an endoscope system according to the present invention will be described in detail with reference to the accompanying drawings.

First Embodiment

Configuration of Endoscope System

Figure 1:
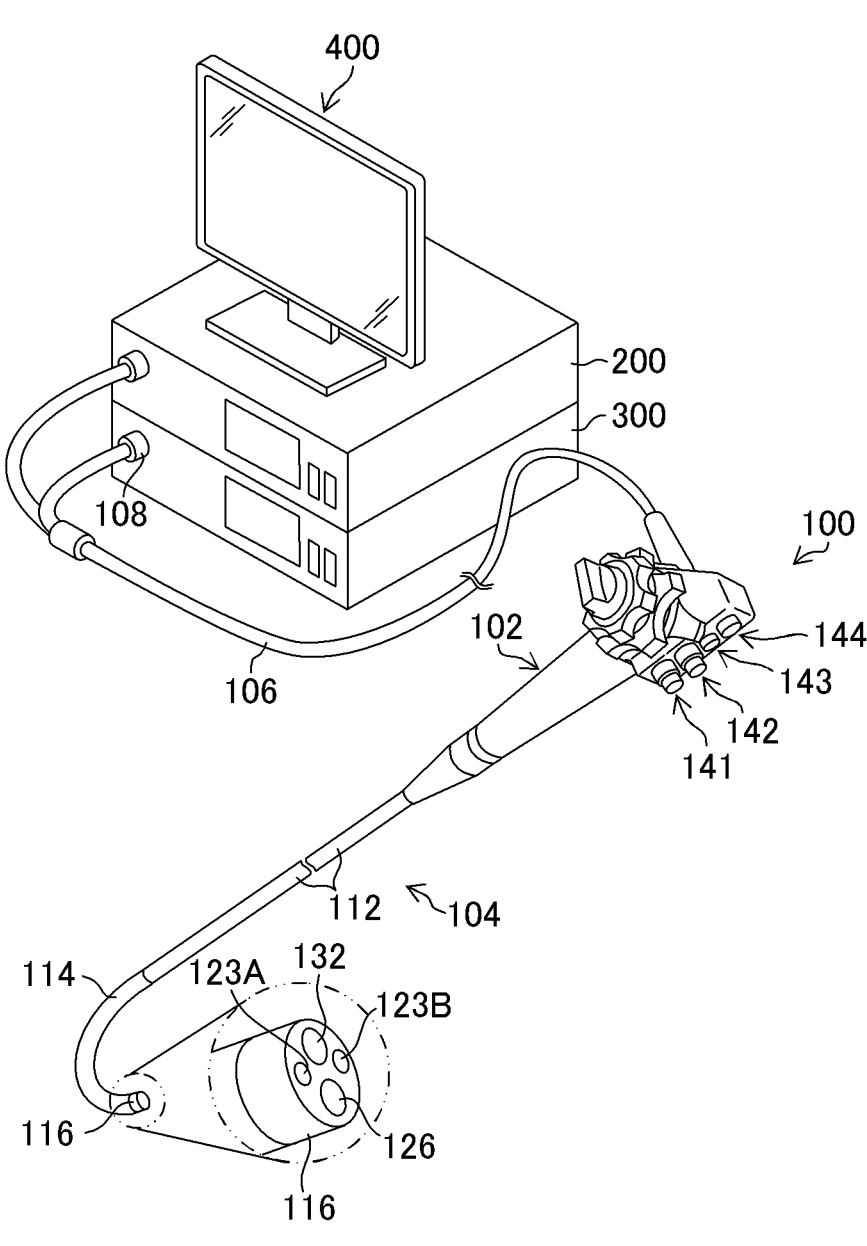
FIG. 1 is a diagram illustrating the configuration of an endoscope system according to a first embodiment.
Figure 2:
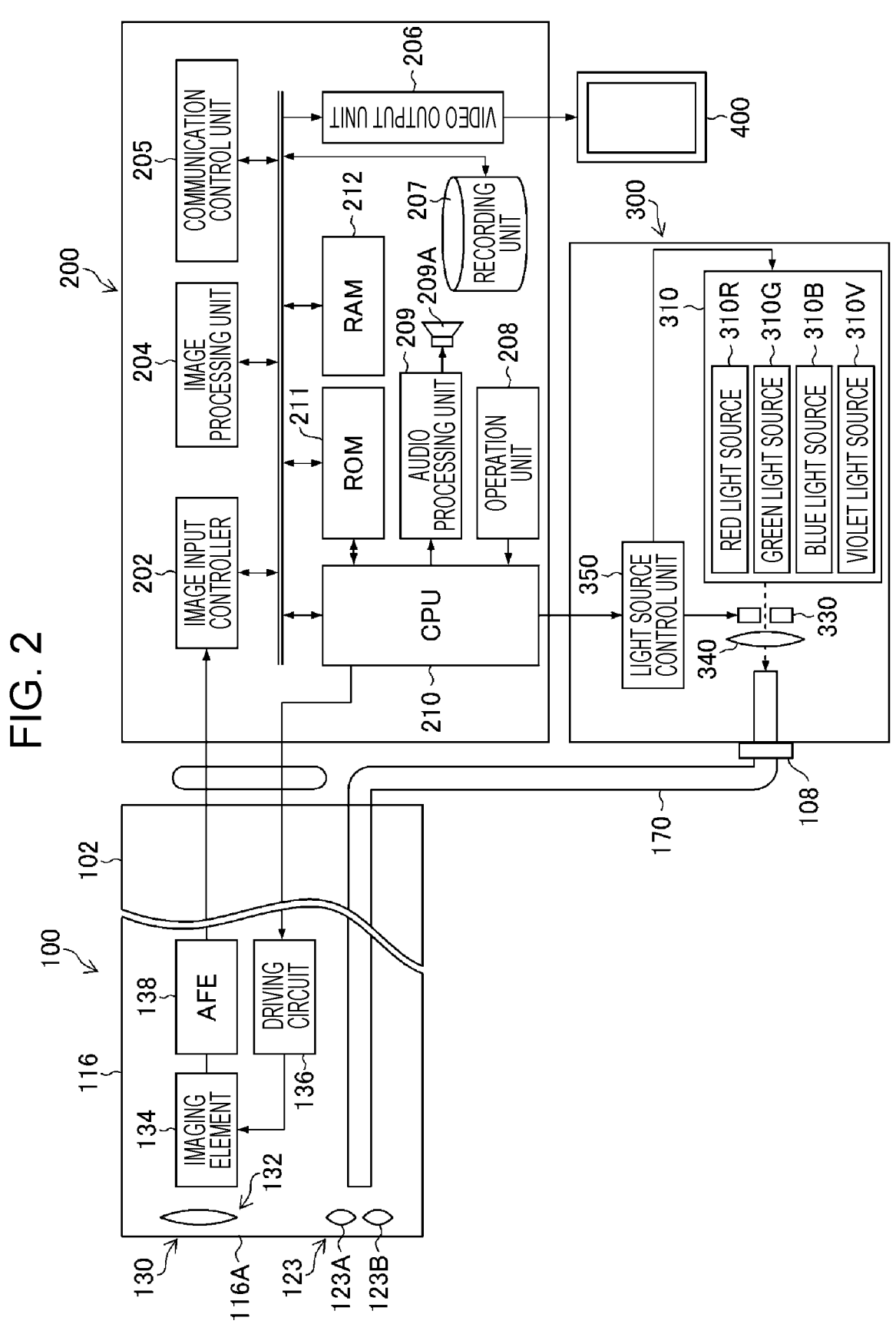
FIG. 2 is another diagram illustrating the configuration of the endoscope system.

FIG. 1 is an external appearance diagram of an endoscope system 10 (an endoscope system, a medical image processing apparatus), and FIG. 2 is a block diagram illustrating the configuration of a main part of the endoscope system 10. As illustrated in FIGS. 1 and 2, the endoscope system 10 is constituted by an endoscope 100 (a medical image acquiring unit, an endoscope), a processor 200 (a medical image processing apparatus, a processor, a medical image acquiring unit, an area recognizing unit, a determining unit, a reporting unit, a reporting control unit, an operation accepting unit, a movement direction estimating unit), a light source apparatus 300 (a light source apparatus), and a monitor 400 (a display apparatus, a display).

Configuration of Endoscope

The endoscope 100 includes a handheld operation section 102 and an insertion section 104 that communicates with the handheld operation section 102. An operator (a user) operates the handheld operation section 102 while grasping it and inserts the insertion section 104 into a body of a subject (a living body) to perform observation. The handheld operation section 102 is provided with an air/water supply button 141, a suction button 142, a function button 143 to which various functions are allocated, and an imaging button 144 for receiving an imaging instruction operation (a still image, a moving image). The insertion section 104 is constituted by a soft part 112, a bending part 114, and a tip rigid part 116, which are arranged in this order from the handheld operation section 102 side. That is, the bending part 114 is connected to a base end side of the tip rigid part 116, and the soft part 112 is connected to a base end side of the bending part 114. The handheld operation section 102 is connected to a base end side of the insertion section 104. The user is able to change the orientation of the tip rigid part 116 in an up, down, left, or right direction by causing the bending part 114 to bend by operating the handheld operation section 102. The tip rigid part 116 is provided with an imaging optical system 130, an illumination unit 123, a forceps port 126, and so forth (see FIGS. 1 and 2).

During observation or treatment, an operation of an operation unit 208 (see FIG. 2) enables white light and/or narrow-band light (one or more of red narrow-band light, green narrow-band light, blue narrow-band light, and violet narrow-band light) to be radiated from illumination lenses 123A and 123B of the illumination unit 123. In addition, an operation of the air/water supply button 141 enables washing water to be ejected from a water supply nozzle that is not illustrated, so that an imaging lens 132 (an imaging lens, an imaging unit) of the imaging optical system 130 and the illumination lenses 123A and 123B can be washed. The forceps port 126 opening in the tip rigid part 116 communicates with a pipe line that is not illustrated, so that a treatment tool that is not illustrated and is for extirpating a tumor or the like can be inserted into the pipe line and necessary treatment can be given to a subject by moving the treatment tool forward or backward as appropriate.

As illustrated in FIGS. 1 and 2, the imaging lens 132 (an imaging unit) is disposed on a distal-end-side surface 116A of the tip rigid part 116. An imaging element 134 (an imaging element, an image acquiring unit) of a complementary metal-oxide semiconductor (CMOS) type, a driving circuit 136, and an analog front end (AFE) 138 (an imaging unit) are disposed behind the imaging lens 132, and these elements output an image signal. The imaging element 134 is a color imaging element and includes a plurality of pixels constituted by a plurality of light-receiving elements arranged in a matrix (arranged two-dimensionally) in a specific pattern arrangement (Bayer arrangement, X-Trans (registered trademark) arrangement, honeycomb arrangement, or the like). Each pixel of the imaging element 134 includes a microlens, a red (R), green (G), or blue (B) color filter, and a photoelectric conversion unit (a photodiode or the like). The imaging optical system 130 is capable of generating a color image from pixel signals of three colors, red, green, and blue, and is also capable of generating an image from pixel signals of any one or two colors among red, green, and blue. The imaging element 134 may be of a charge coupled device (CCD) type. Each pixel of the imaging element 134 may further include a violet color filter corresponding to a violet light source 310V and/or an infrared filter corresponding to an infrared light source.

An optical image of a subject is formed on a light-receiving surface (an imaging surface) of the imaging element 134 by the imaging lens 132, converted into an electric signal, output to the processor 200 through a signal cable that is not illustrated, and converted into a video signal. Accordingly, an endoscopic image (an image, a medical image) of the photographic subject is displayed on the monitor 400, which is connected to the processor 200.

The illumination lenses 123A and 123B of the illumination unit 123 are provided next to the imaging lens 132 on the distal-end-side surface 116A of the tip rigid part 116. An emission end of a light guide 170, which will be described below, is disposed behind the illumination lenses 123A and 123B. The light guide 170 extends through the insertion section 104, the handheld operation section 102, and a universal cable 106, and an incidence end of the light guide 170 is located in a light guide connector 108.

A user performs imaging (under control of a medical image acquiring unit 220) at a determined frame rate while inserting or removing the endoscope 100 (the insertion section 104) having the above-described configuration into or from a living body as a subject, thereby being capable of sequentially capturing time-series images of the inside of the living body.

Configuration of Light Source Apparatus

As illustrated in FIG. 2, the light source apparatus 300 is constituted by a light source 310 for illumination, a diaphragm 330, a condenser lens 340, a light source control unit 350, and so forth, and causes observation light to enter the light guide 170. The light source 310 includes a red light source 310R, a green light source 310G, a blue light source 310B, and the violet light source 310V that radiate red narrow-band light, green narrow-band light, blue narrow-band light, and violet narrow-band light, respectively, and is capable of radiating red narrow-band light, green narrow-band light, blue narrow-band light, and violet narrow-band light. The illuminance of observation light from the light source 310 is controlled by the light source control unit 350, which is capable of changing (increasing or decreasing) the illuminance of observation light or stopping illumination as necessary.

The light source 310 is capable of emitting red narrow-band light, green narrow-band light, blue narrow-band light, and violet narrow-band light in any combination. For example, the light source 310 is capable of simultaneously emitting red narrow-band light, green narrow-band light, blue narrow-band light, and violet narrow-band light to radiate white light (normal light) as observation light, and is also capable of emitting any one or two of red narrow-band light, green narrow-band light, blue narrow-band light, and violet narrow-band light to radiate narrow-band light (special light). The light source 310 may further include an infrared light source that radiates infrared light (an example of narrow-band light). Alternatively, with use of a light source that radiates white light and a filter that allows white light and each narrow-band light to pass therethrough, white light or narrow-band light may be radiated as observation light.

Wavelength Range of Light Source

The light source 310 may be a light source that generates light in a white range or light in a plurality of wavelength ranges as the light in the white range, or may be a light source that generates light in a specific wavelength range narrower than the white wavelength range. The specific wavelength range may be a blue range or green range in a visible range, or may be a red range in the visible range. In a case where the specific wavelength range is the blue range or green range in the visible range, the specific wavelength range may include a wavelength range of 390 nm or more and 450 nm or less or a wavelength range of 530 nm or more and 550 nm or less, and the light in the specific wavelength range may have a peak wavelength in the wavelength range of 390 nm or more and 450 nm or less or the wavelength range of 530 nm or more and 550 nm or less. In a case where the specific wavelength range is the red range in the visible range, the specific wavelength range may include a wavelength range of 585 nm or more and 615 nm or less or a wavelength range of 610 nm or more and 730 nm or less, and the light in the specific wavelength range may have a peak wavelength in the wavelength range of 585 nm or more and 615 nm or less or the wavelength range of 610 nm or more and 730 nm or less.

The above-described the specific wavelength range may include a wavelength range in which a light absorption coefficient is different between oxyhemoglobin and deoxyhemoglobin, and the light in the specific wavelength range may have a peak wavelength in the wavelength range in which the light absorption coefficient is different between oxyhemoglobin and deoxyhemoglobin. In this case, the specific wavelength range may include a wavelength range of 400±10 nm, a wavelength range of 440±10 nm, a wavelength range of 470±10 nm, or a wavelength range of 600 nm or more and 750 nm or less, and the light in the specific wavelength range may have a peak wavelength in the wavelength range of 400±10 nm, the wavelength range of 440±10 nm, the wavelength range of 470±10 nm, or the wavelength range of 600 nm or more and 750 nm or less.

The wavelength range of the light generated by the light source 310 may include a wavelength range of 790 nm or more and 820 nm or less or a wavelength range of 905 nm or more and 970 nm or less, and the light generated by the light source 310 may have a peak wavelength in the wavelength range of 790 nm or more and 820 nm or less or the wavelength range of 905 nm or more and 970 nm or less.

Alternatively, the light source 310 may include a light source that radiates excitation light whose peak is 390 nm or more and 470 nm or less. In this case, a medical image (an inside-of-living-body image) having information about fluorescence emitted by a fluorescent substance in a subject (a living body) can be acquired. In the case of acquiring a fluorescence image, a pigment for a fluorescence method (fluorescein, acridine orange, or the like) may be used.

It is preferable that the type of the light source 310 (a laser light source, a xenon light source, a light-emitting diode (LED) light source, or the like), the wavelength of the light source 310, the presence or absence of a filter for the light source 310, and so forth be determined in accordance with the type, area, purpose of observation, or the like of a photographic subject. It is also preferable that, during observation, the wavelengths of observation light be combined and/or switched in accordance with the type, area, purpose of observation, or the like of a photographic subject. In the case of switching the wavelength, for example, a disc-shaped filter (a rotary color filter) that is disposed in front of the light source and that is provided with a filter for transmitting or blocking light of a specific wavelength may be rotated to switch the wavelength of light to be radiated.

The imaging element used to carry out the present invention is not limited to a color imaging element in which color filters are disposed for the individual pixels, such as the imaging element 134, and may be a monochrome imaging element. In the case of using a monochrome imaging element, imaging can be performed in a frame sequential (color sequential) manner by sequentially switching the wavelength of observation light. For example, the wavelength of outgoing observation light may be sequentially switched among violet, blue, green, and red, or wide-band light (white light) may be radiated and the wavelength of outgoing observation light may be switched by using a rotary color filter (red, green, blue, violet, and the like). Alternatively, one or a plurality of types of narrow-band light (green, blue, violet, and the like) may be radiated and the wavelength of outgoing observation light may be switched by using a rotary color filter (green, blue, violet, and the like). The narrow-band light may be infrared light of two or more different wavelengths (first narrow-band light and second narrow-band light).

As a result of connecting the light guide connector 108 (see FIGS. 1 and 2) to the light source apparatus 300, observation light radiated by the light source apparatus 300 is transmitted through the light guide 170 to the illumination lenses 123A and 123B and is radiated from the illumination lenses 123A and 123B to an observation range.

Configuration of Processor

The configuration of the processor 200 will be described with reference to FIG. 2. In the processor 200, an image input controller 202 receives an image signal output from the endoscope 100, an image processing unit 204 (a medical image processing unit, a processor) performs necessary image processing thereon, and a video output unit 206 outputs a resulting image signal. Accordingly, an observation image (an inside-of-living-body image) is displayed on the monitor 400 (a display apparatus). These processing operations are performed under control by a central processing unit (CPU) 210 (a processor). A communication control unit 205 controls communication, for acquiring a medical image, with a hospital information system (HIS), a hospital local area network (LAN), and/or an external system or network that are not illustrated.

Functions of Image Processing Unit

Figure 3:
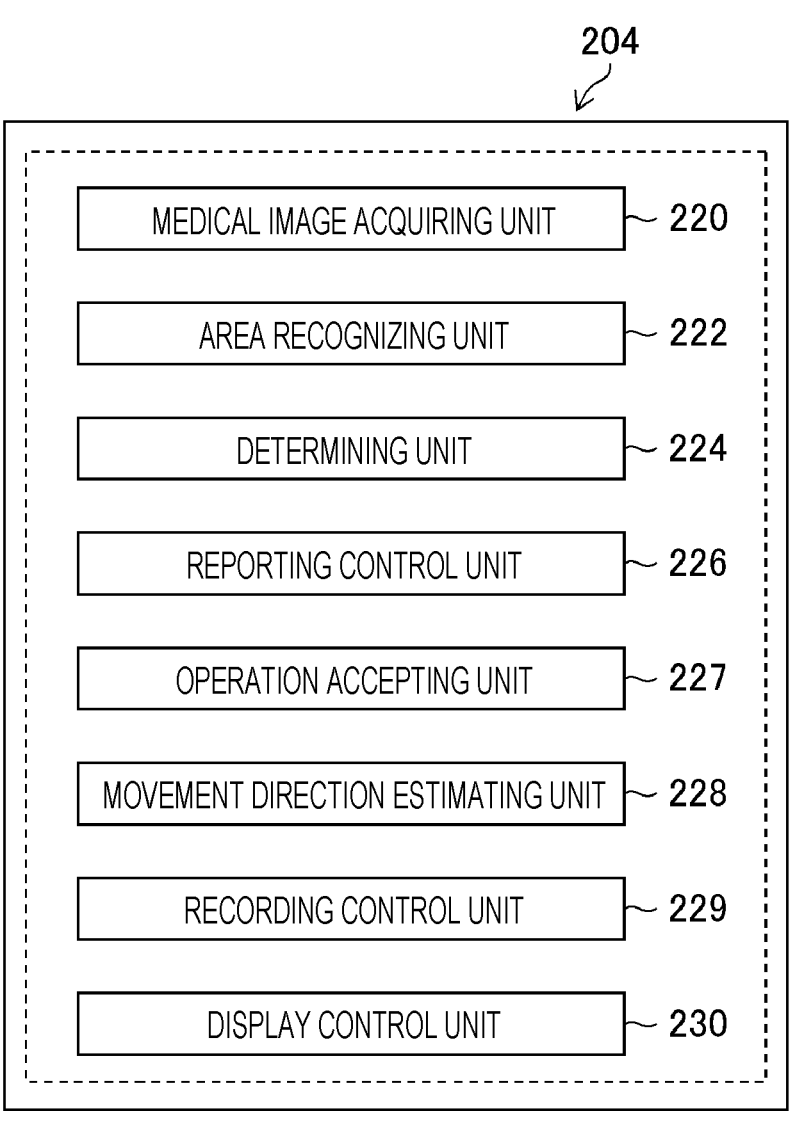
FIG. 3 is a functional block diagram of an image processing unit.

FIG. 3 is a functional block diagram of the image processing unit 204. The image processing unit 204 includes the medical image acquiring unit 220 (a medical image acquiring unit, an image acquiring unit), an area recognizing unit 222 (an area recognizing unit), a determining unit 224 (a determining unit), a reporting control unit 226 (a reporting control unit), an operation accepting unit 227 (an operation accepting unit), a movement direction estimating unit 228 (a movement direction estimating unit), a recording control unit 229 (a recording control unit), and a display control unit 230 (a display control unit). Processing using these functions will be described below in detail.

The image processing unit 204 is capable of performing, with the above-described functions, calculation of a feature quantity of a medical image, processing of emphasizing or reducing a component of a specific frequency band, and processing of emphasizing or deemphasizing a specific target (a region of interest, blood vessels at a desired depth, or the like). The image processing unit 204 may include a special-light image acquiring unit that acquires a special-light image having information about a specific wavelength range on the basis of a normal-light image that is acquired by radiating light in the white range or light in a plurality of wavelength ranges as the light in the white range. In this case, a signal in the specific wavelength range can be acquired through computation based on color information of RGB (R: red, G: green, B: blue) or CMY (C: cyan, M: magenta, Y: yellow) included in the normal-light image. In addition, the image processing unit 204 may include a feature quantity image generating unit that generates a feature quantity image through computation based on at least one of a normal-light image that is acquired by radiating light in the white range or light in a plurality of wavelength ranges as the light in the white range or a special-light image that is acquired by radiating light in a specific wavelength range, and may acquire and display the feature quantity image as a medical image. The above-described processing is performed under control by the CPU 210.

Implementation of Functions by Various Types of Processors

The functions of the above-described units of the image processing unit 204 can be implemented by using various types of processors and a recording medium. The various types of processors include, for example, a central processing unit (CPU) which is a general-purpose processor that executes software (program) to implement various functions. Also, the various types of processors include a graphics processing unit (GPU) which is a processor dedicated to image processing, and a programmable logic device (PLD) which is a processor whose circuit configuration is changeable after manufacturing, such as a field programmable gate array (FPGA). In the case of performing learning and recognition of images as in the present invention, the configuration using a GPU is effective. Furthermore, the various types of processors include a dedicated electric circuit which is a processor having a circuit configuration designed exclusively for executing specific processing, such as an application specific integrated circuit (ASIC).

The function of each unit may be implemented by one processor or may be implemented by a plurality of processors of the same type or different types (for example, a combination of a plurality of FPGAs, a combination of a CPU and an FPGA, or a combination of a CPU and a GPU). A plurality of functions may be implemented by one processor. A first example of implementing a plurality of functions by one processor is that a combination of one or more CPUs and software constitute one processor and the one processor implements the plurality of functions, as represented by a computer. A second example is that a processor that implements the functions of an entire system by one integrated circuit (IC) chip is used, as represented by a system on chip (SoC). In this way, various functions are configured as a hardware structure by using one or more of the above-described various types of processors. Furthermore, the hardware structure of the various types of processors is, more specifically, electric circuitry formed by combining circuit elements such as semiconductor elements. The electric circuitry may be electric circuitry that implements the above-described functions by using logical disjunction, logical conjunction, logical negation, exclusive disjunction, and logical operation as a combination thereof.

When the above-described processor or electric circuitry executes the software (program), the code of the software to be executed that is readable by a computer (for example, the various types of processors or electric circuitry constituting the image processing unit 204, and/or a combination thereof) is stored in a non-transitory recording medium, such as a read only memory (ROM) 211, and the computer refers to the software. The software stored in the non-transitory recording medium includes a program for executing a method for operating the medical image processing apparatus according to the present invention and data to be used for the execution (data about acquisition of a medical image, data used to specify a reporting condition and a reporting mode, a parameter used in a recognizing unit, and so forth). The code may be recorded on a non-transitory recording medium, such as a magneto-optical recording device of various types or a semiconductor memory, instead of the ROM 211. In the processing using the software, a random access memory (RAM) 212 may be used as a transitory storage region, for example, and data stored in an electrically erasable and programmable read only memory (EEPROM) that is not illustrated can be referred to, for example. A recording unit 207 may be used as a "non-transitory recording medium".

The read only memory (ROM) 211 is a nonvolatile storage element (a non-transitory recording medium) and stores a computer-readable code of a program that causes the CPU 210 and/or the image processing unit 204 (a computer) to execute various image processing methods (including the method for operating the medical image processing apparatus according to the present invention). The random access memory (RAM) 212 is a storage element for temporary storage in various processing operations and can be used as a buffer when acquiring an image. An audio processing unit 209 outputs a message (audio) about medical image processing, area recognition, reporting, or the like from a speaker 209A (a reporting unit, a speaker) under control by the CPU 210 and the image processing unit 204.

Operation Unit

The operation unit 208 can be constituted by devices such as a keyboard and a mouse that are not illustrated. A user is able to provide an instruction to execute medical image processing or designate a condition necessary for the execution (for example, setting of a reporting condition and a reporting mode described below) via the operation unit 208 (an operation accepting unit). An operation via the operation unit 208 includes setting of a reporting condition and a reporting mode (see FIG. 8) and an operation of indicating that acquisition of a medical image of a plurality of areas to be imaged has been ended. The above-described operation accepting unit 227 accepts a user operation via the operation unit 208. In accordance with the accepted operation, processing is performed by the CPU 210 and individual units of the image processing unit 204.

Information Stored in Recording Unit

Figure 4:
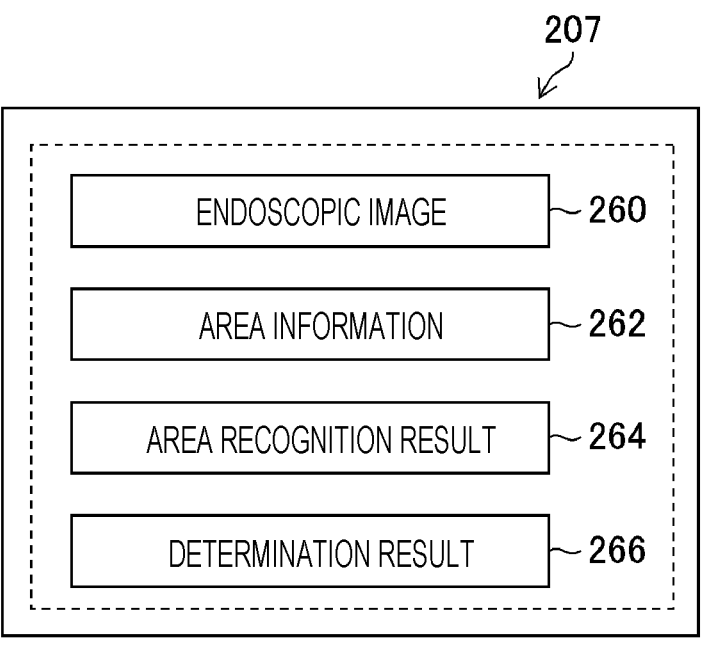
FIG. 4 is a diagram illustrating information stored in a recording unit.

As illustrated in FIG. 4, the recording unit 207 (a recording device, a memory, a non-transitory recording medium) stores an endoscopic image 260 (an endoscopic image, a medical image), area information 262 (area information; information indicating a plurality of areas to be imaged in a photographic subject), an area recognition result 264 (a recognition result of an area of a photographic subject in a medical image), a determination result 266 (a determination result of a not-yet-imaged area among a plurality of areas to be imaged), and so forth. The area information 262 may have a form of an image or another form such as a list form made up of characters and numerals (for example, "thoracic esophagus 1", "central gastric body B", "lesser-curvature-side-portion of angulus").

Recognizing Unit Using Neural Network

In the first embodiment, the area recognizing unit 222 can be constituted by using a trained model (a model trained by using an image set constituted by captured images of a living body), such as a neural network. Hereinafter, a description will be given of a configuration of the case of performing multi-class classification (individual classes correspond to different areas) by using a convolutional neural network (CNN) as a neural network.

Example of Configuration of Recognizing Unit

Figures 5A, 5B:
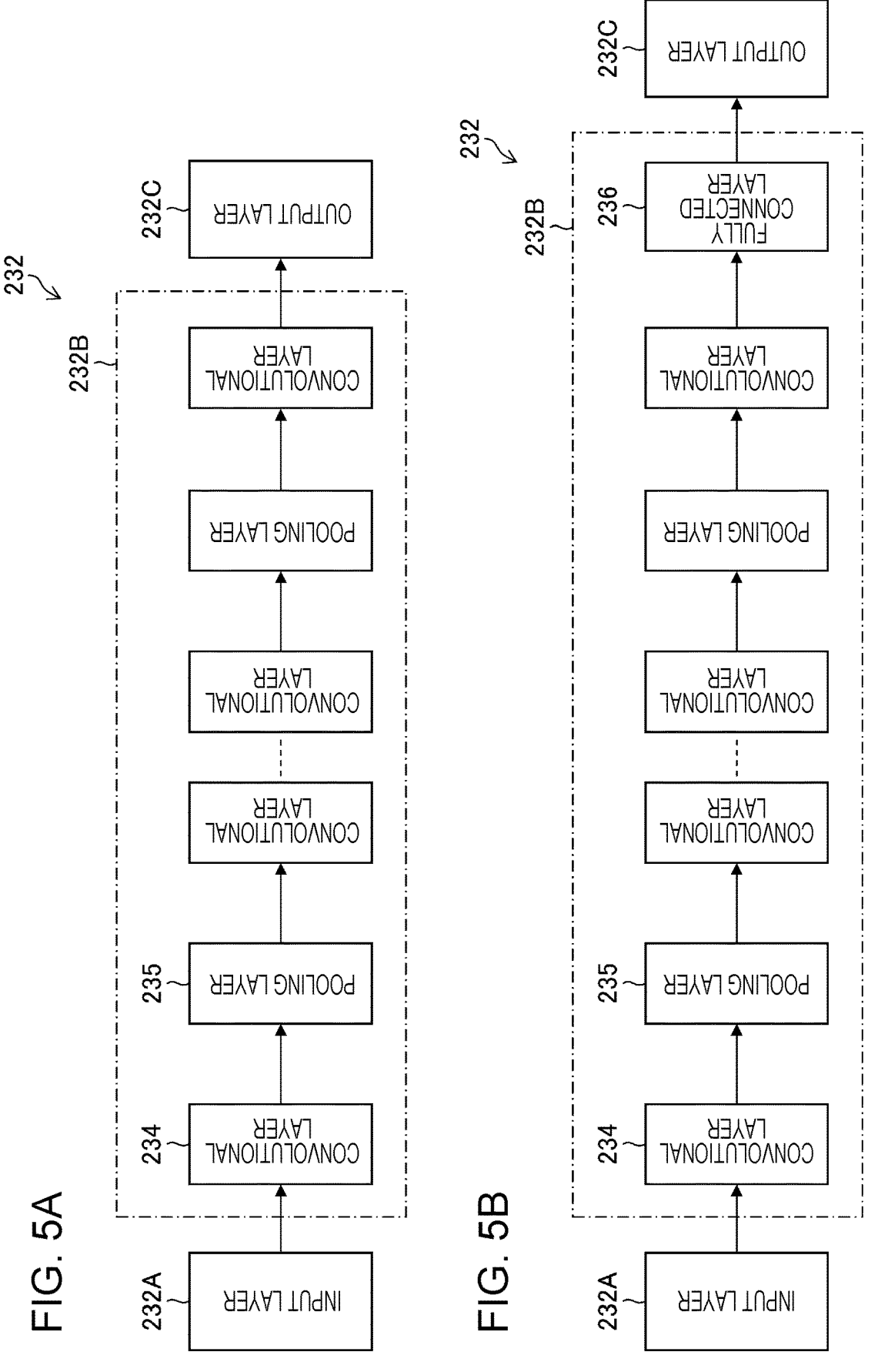
FIGS. 5A and 5B are diagrams illustrating configuration examples of a convolutional neural network.

FIGS. 5A and 5B are diagrams illustrating configurations of a CNN 232 (neural network). In the example illustrated in FIG. 5A, the CNN 232 has an input layer 232A (an input unit), an intermediate layer 232B, and an output layer 232C. The input layer 232A receives an endoscopic image (medical image) acquired by the medical image acquiring unit 220 and outputs a feature quantity. The intermediate layer 232B includes convolutional layers 234 and pooling layers 235, and receives the feature quantity output from the input layer 232A and calculates another feature quantity. These layers have a structure in which a plurality of "nodes" are connected by "edges". Weighting coefficients applied to an input image are associated with the nodes and edges and are stored in a weighting coefficient storage unit that is not illustrated. The values of the weighting coefficients change as learning progresses.

Processing in Intermediate Layer

The intermediate layer 232B calculates a feature quantity through convolutional operation and pooling processing. The convolutional operation performed in the convolutional layer 234 is processing of acquiring a feature map through convolutional operation using a filter, and plays a role in feature extraction such as edge extraction from an image. As a result of the convolutional operation using a filter, one-channel (one) "feature map" is created for one filter. The size of the "feature map" is reduced as convolution is performed in each layer in the case of being scaled down by convolution. The pooling processing performed in the pooling layer 235 is processing of reducing (or enlarging) the feature map output through the convolutional operation to create a new feature map, and plays a role in giving robustness so that the extracted feature is not affected by parallel movement or the like. The intermediate layer 232B can be constituted by one or a plurality of layers that perform these processing operations. The CNN 232 may be configured without a pooling layer 235.

The CNN 232 may include a fully connected layer 236 as in the example illustrated in FIG. 5B. The layer configuration of the CNN 232 is not limited to the configuration in which the convolutional layers 234 and the pooling layers 235 are alternately arranged, and may include a plurality of consecutive convolutional layers 234 or pooling layers 235 (for example, convolutional layers 234).

Figure 6:
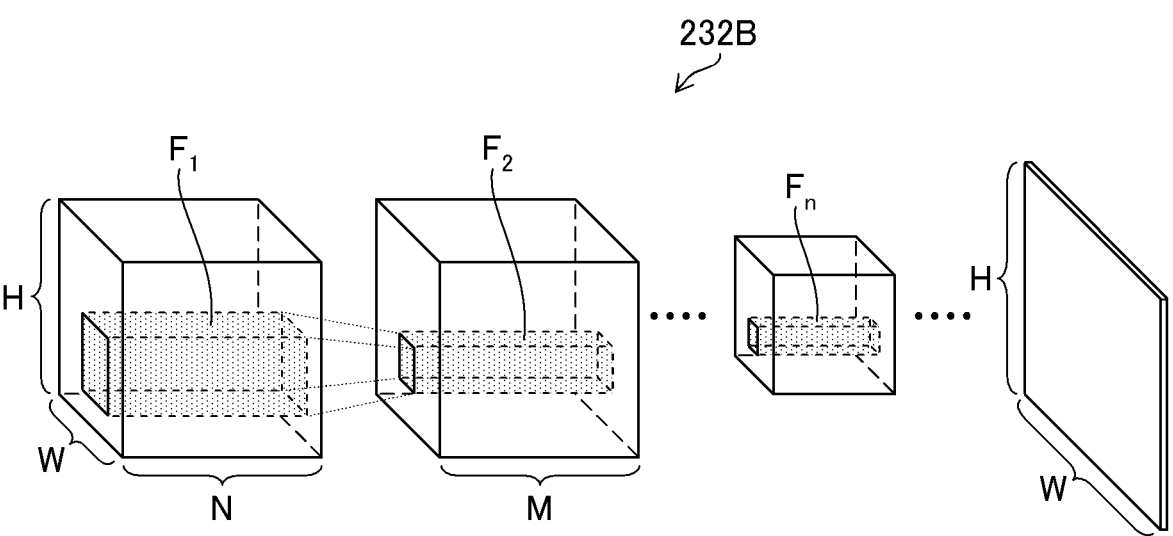
FIG. 6 is a diagram illustrating a state of convolutional processing using filters.

FIG. 6 is a schematic diagram illustrating an example configuration of the intermediate layer 232B of the CNN 232 illustrated in FIGS. 5A and 5B. In the first convolutional layer of the intermediate layer 232B, convolutional operation of an image set constituted by a plurality of medical images (a learning image set in the case of learning, and an area recognition image set in the case of area recognition) and a filter $F_1$ is performed. The image set is constituted by N (N-channel) images each having an image size in which the height is represented by H and the width is represented by W. In the case of inputting normal-light images, the images constituting an image set are three-channel images of red (R), green (G), and blue (B). The filter $F_1$ convoluted with this image set has a filter size of 5×5×N in the case of the filter having size 5 (5×5), for example, because the image set has N channels (N images). As a result of convolutional operation using the filter $F_1$, one-channel (one) "feature map" is created for one filter $F_1$. A filter $F_2$ used in the second convolutional layer has a filter size of 3×3×M in the case of the filter having size 3 (3×3), for example.

As in the first convolutional layer, in the second to n-th convolutional layers, convolutional operations using filters $F_2$ to $F_n$ are performed, respectively. The size of the "feature map" in the n-th convolutional layer is smaller than the size of the "feature map" in the second convolutional layer because scaling-down is performed in the convolutional layers or pooling layers in the preceding stages.

In the layers of the intermediate layer 232B, lower-order feature extraction (extraction of edges or the like) is performed in a convolutional layer near the input side, and higher-order feature extraction (extraction of features about the shape, structure, and the like of a recognition target) is performed near the output side.

The intermediate layer 232B may include a layer for performing batch normalization in addition to the convolutional layers 234 and the pooling layers 235. Batch normalization processing is the processing of normalizing a data distribution in units of mini batches for performing learning, and plays a role in quickly performing learning, reducing dependency on an initial value, suppressing overtraining, and so forth.

The output layer 232C outputs the feature quantity calculated by the intermediate layer 232B in a form appropriate for area recognition. The output layer 232C may include a fully connected layer.

Individual Processes of Medical Image Processing Method

Figure 7:
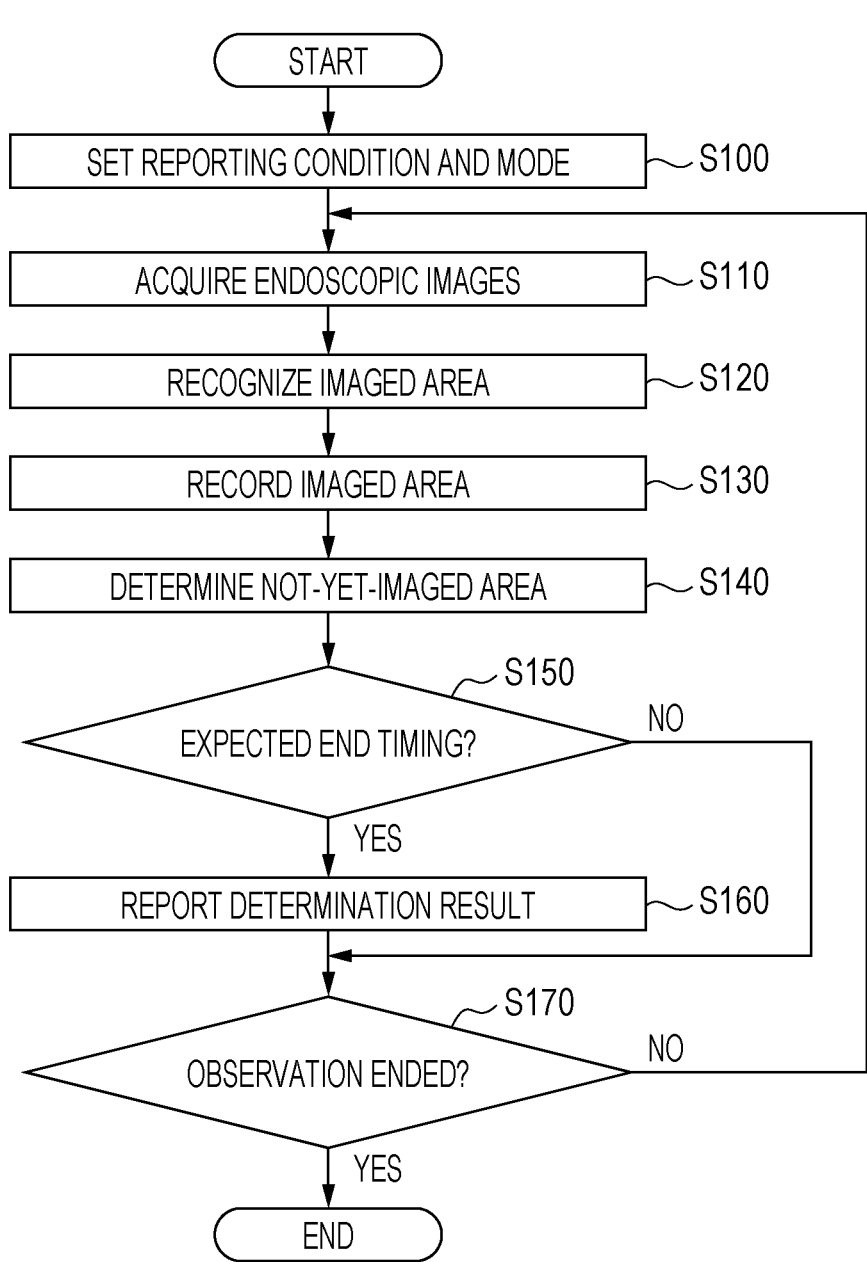
FIG. 7 is a flowchart illustrating a procedure of a medical image processing method according to the first embodiment.

FIG. 7 is a flowchart illustrating an overview of a process of a medical image processing method (a method for operating a medical image processing apparatus) according to the first embodiment. It is assumed that learning of the CNN 232 using learning data has been executed.

Setting of Reporting Condition and Reporting Mode

The image processing unit 204 (the reporting control unit 226) sets a reporting condition and a reporting mode in accordance with a user operation performed via the operation unit 208 (step S100: a reporting condition setting step, a reporting mode setting step). The user is able to perform a setting operation via a screen 700 (displayed on the monitor 400) illustrated in FIG. 8.

The screen 700 has regions 702 to 712 in which radio buttons are disposed, a region 714 in which a pull-down menu is disposed, and a region 716 in which a numerical value input field is disposed. The user is able to set whether to perform reporting (ON or OFF; the region 702) by operating a radio button. The user is also able to set "whether to perform reporting" (the region 702), "whether to perform reporting by screen display" (the region 704), whether to display a reporting screen in an initial state" (the region 706; see the examples in FIGS. 10A to 11D), and "whether to perform reporting by audio output (audio signal)" (the region 708) by operating radio buttons. Furthermore, the user is able to set "whether to perform reporting at a timing at which the organ of the photographic subject in a medical image is switched" (the region 710), and "whether to perform reporting at a timing at which a medical image of the photographic subject in a predetermined area (a so-called landmark) is captured" (the region 712) by operating radio buttons. In a case where the radio button in the region 712 is "ON", the user is able to select an area as a landmark by operating the pull-down menu in the region 714. In the example in FIG. 8, "esophagogastric junction (EGJ)" is selected as a landmark, but the landmark may be another area (for example, the pharynx).

The above-described "timing at which the organ of the photographic subject in a medical image is switched" and "timing at which a medical image of the photographic subject in a predetermined area is captured" are examples of an "expected end timing" (the timing at which acquisition of a medical image of a plurality of areas to be imaged is expected to have been ended) in the present invention.

Furthermore, the user is able to set an "elapsed time from start to end of reporting (from start of a reporting state to switching to a non-reporting state)" ("predesignated time") by inputting a numerical value in the region 716. After the time (seconds) input to the region 716 has elapsed, the reporting control unit 226 switches reporting by the monitor 400 and/or the speaker 209A from a reporting state to a non-reporting state (stops or ends reporting). In the example in FIG. 8, the time from start to end of reporting is 1.0 second. The numerical value may be input by selecting a determined numerical value from a pull-down menu. With such switching to the non-reporting state, assistance can be finished according to necessity of the user, and excessive assistance can be suppressed. The reporting control unit 226 may decrease (reduce) a reporting intensity after the designated time has elapsed, in addition to or instead of ending reporting.

In this way, in the endoscope system 10 (a medical image processing apparatus, an endoscope system), the user is able to set a reporting condition and a reporting mode according to necessity. The reporting control unit 226 performs reporting (assistance) in accordance with the settings, and thus excessive reporting can be suppressed. The above-described example is an example of settings, and another item (reporting by light or vibration or the like) may be set. The settings of a reporting condition and a reporting mode may be made not only at start of medical image processing but also at any timing during the processing. Furthermore, settings of a reporting condition and a reporting mode may be automatically made by the endoscope system 10 independently of a user operation.

Acquisition of Endoscopic Image

The medical image acquiring unit 220 acquires time-series endoscopic images (medical images) (step S110: an image acquisition step). The medical image acquiring unit 220 may acquire an endoscopic image captured by the endoscope 100, or may acquire the endoscopic image 260 stored in the recording unit 207. In a case where the medical image acquiring unit 220 acquires an endoscopic image captured by the endoscope 100, the recording control unit 229 is capable of storing the acquired image as the endoscopic image 260 in the recording unit 207.

Recognition of Imaged Area

The area recognizing unit 222 (an area recognizing unit, a processor) recognizes an area (imaged area) of a photographic subject in the endoscopic image acquired in step S110 by using the above-described CNN 232 (step S120: an area recognition step). The area may be, for example, in the case of the esophagus, the cervical esophagus, the thoracic esophagus, or the abdominal esophagus. The thoracic esophagus may further be classified into the upper thoracic esophagus, the middle thoracic esophagus, or the lower thoracic esophagus. In the case of the stomach, the area may be the cardia, the fornix (fundus), the gastric body, the angulus, the antrum, the prepyloric region, or the pyloric ring. The gastric body may further be classified into an upper portion, a middle portion, or a lower portion. The gastric body may be classified into the lesser curvature, the anterior wall, the greater curvature, or the posterior wall in a circumference direction.

The area recognizing unit 222 (a processor) may determine that "an area has been recognized" in response to at least one of a condition that a specific photographic subject is continuously in an endoscopic image (medical image) for a predetermined time or more, a condition that a specific photographic subject is in a determined region (for example, center) of an endoscopic image, a condition that a specific photographic subject is in an endoscopic image in a determined size or more, or a condition that a specific photographic subject has a determined in-focus degree or more in an endoscopic image being satisfied.

Recording of Imaged Area

The recoding control unit 229 records information on the imaged area (an area recognition result) as the area recognition result 264 in the recording unit 207 (step S130: a recognition result recording step). Preferably, the recording control unit 229 records the area recognition result in association with the endoscopic image. The recording control unit 229 may record the area recognition result in the above-described list form.

Determination of Not-Yet-Imaged Area

The determining unit 224 compares the area recognized in step S130 (the area recognition result 264) with an area indicated by the area information 262, and determines an area that has not been imaged (a not-yet-imaged area) among the plurality of areas to be imaged (step S140: a determination step). The determining unit 224 is capable of determining, for example, the presence or absence of a not-yet-imaged area, and/or which area has not been imaged. The determining unit 224 may perform determination every time one or a plurality of images are acquired, or may perform determination every time a designated time elapses.

Reporting of Determination Result at Expected End Timing

The reporting control unit 226 determines whether an expected end timing, at which acquisition of an endoscopic image (medical image) of a plurality of areas to be imaged is expected to have been ended, has come (step S150: a reporting step). For example, a timing at which an area as an observation target is changed from one organ to another organ in a recognition result (for example, a timing of change from the esophagus to the stomach, the setting is made in the region 710 in the example in FIG. 8), and a timing at which a medical image of a photographic subject in a predetermined area is acquired (a timing at which an image of a landmark is acquired, the setting is made in the regions 712 and 714 in the example in FIG. 8) can be regarded as the expected end timing. Also, a timing at which a user operation indicating the end of imaging for a determined range is accepted (a timing at which the operation accepting unit 227 accepts a user operation via the operation unit 208), that is, a timing at which the user recognizes that "imaging has completed", may be regarded as the "expected end timing". Alternatively, the reporting control unit 226 may determine that the expected end timing has come, when a predetermined number of images have been captured or when an imaging time has ended. At the "expected end timing", it is sufficient that end of acquisition of an endoscopic image be expected (there is a possibility), and the acquisition need not actually be ended.

The movement direction estimating unit 228 (a movement direction estimating unit) may estimate a movement direction (insertion of removal) of the endoscope 100 on the basis of a movement vector of a photographic subject, for example, and a timing at which the movement direction is changed from insertion (forward direction) to removal (backward direction) may be regarded as an "expected end timing". Also, a timing at which the user reverses the direction of the tip portion of the endoscope 100 to perform a so-called "looking up" (a timing at which the endoscope 100 is seen in an endoscopic image) may be regarded as an "expected end timing".

Figure 8:
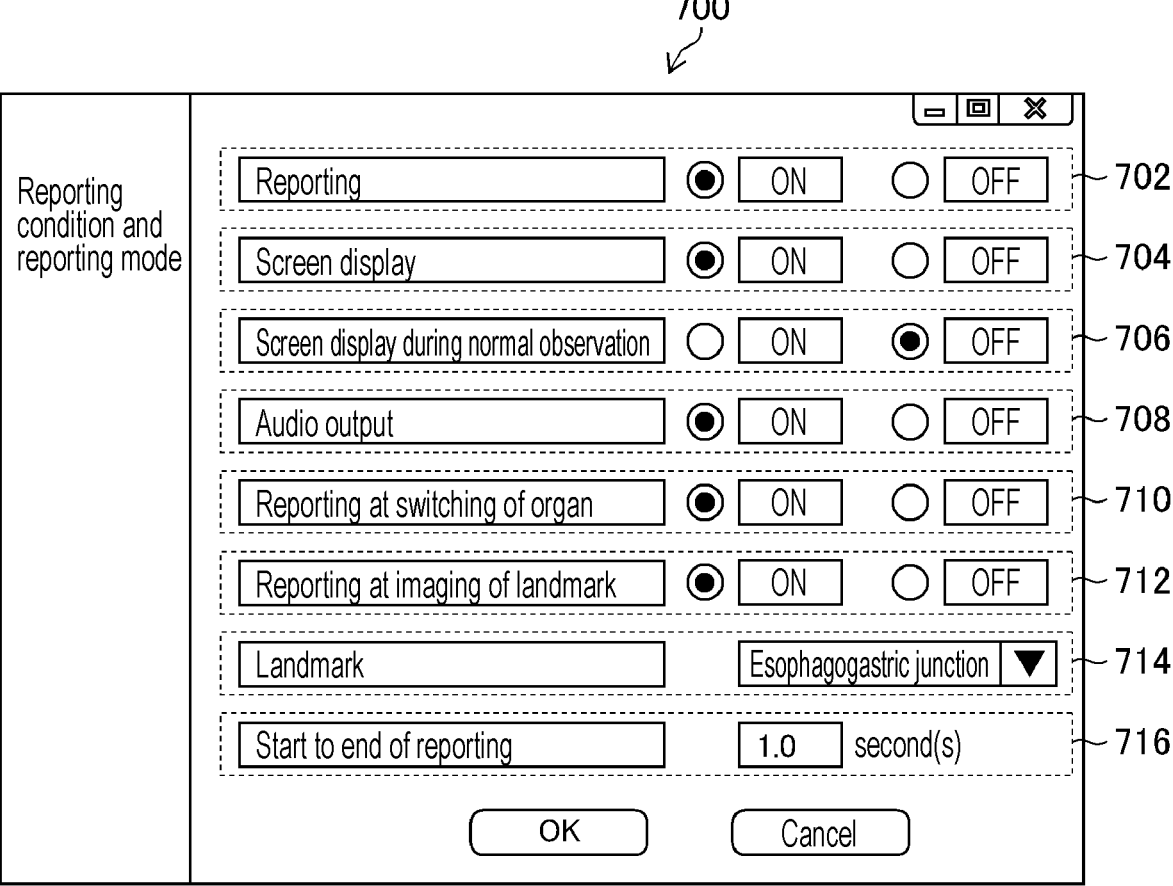
FIG. 8 is a diagram illustrating an example of a setting screen for a reporting condition and a reporting mode.
Figure 9A:
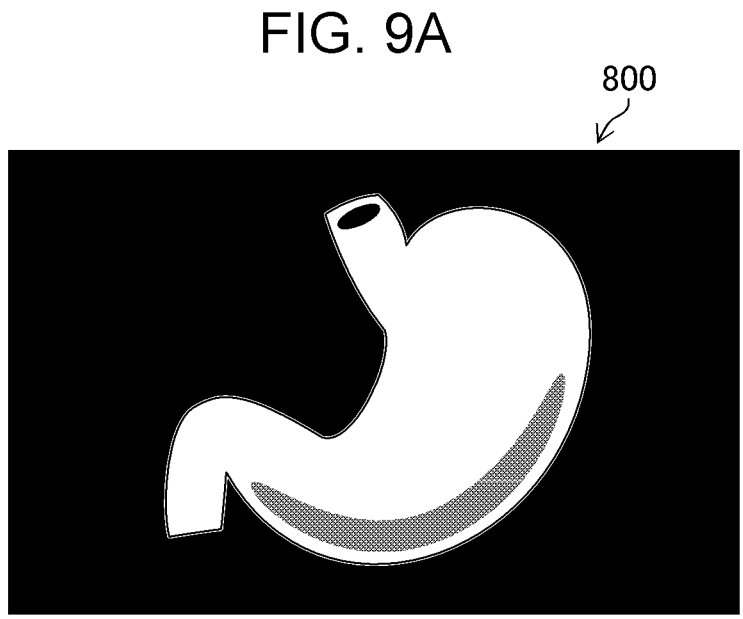
FIGS. 9A and 9B are diagrams illustrating an example of a method for reporting a determination result.
Figure 9B:
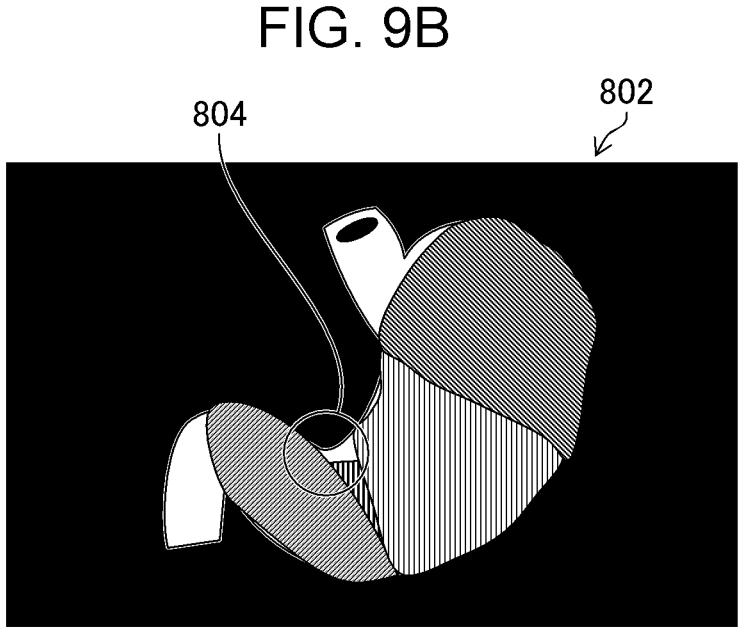

If the expected end timing has come (YES in step S150), the reporting control unit 226 reports the determination result by using the monitor 400 (a reporting unit, a display) and/or the speaker 209A (a reporting unit, a speaker) (step S160: a reporting step). The reporting mode is based on the settings made in step S100 (see the example in FIG. 8). FIGS. 9A and 9B are diagrams illustrating an example of reporting about the stomach. FIG. 9A is a diagram illustrating a state before observation starts (all the areas have not been observed), and the entire region of an image 800 showing a schematic diagram of the stomach is not colored (not shaded). On the other hand, FIG. 9B is a diagram illustrating a reporting state at an expected end timing. In an image 802, observed areas (the fornix, the gastric body, the antrum, the prepyloric region, and the greater-curvature-side-portion of angulus) are color-displayed, whereas an unobserved area (lesser-curvature-side-portion of angulus) is not colored. A symbol (circle 804) surrounding the unobserved area is attached. The schematic diagram of an organ (esophagus, stomach, or the like) may be a three-dimensional model or a development diagram.

The reporting control unit 226 may make the schematic diagram colored during normal observation, and may make an observed area uncolored (or faint-colored) at the time of reporting. Alternatively, an observed area and an unobserved area may be given different colors, the color may be changed at a timing of reporting, or an unobserved area may be blinked.

Figure 10A:
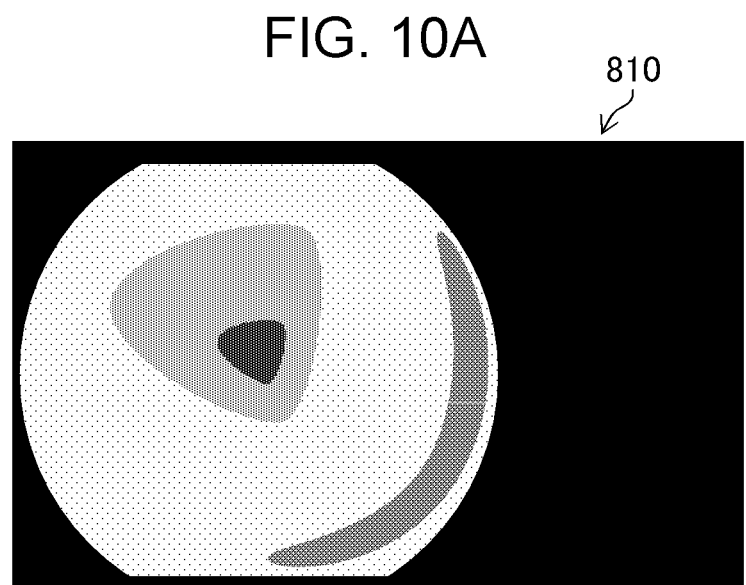
FIGS. 10A and 10B are other diagrams illustrating an example of a method for reporting a determination result.
Figure 10B:
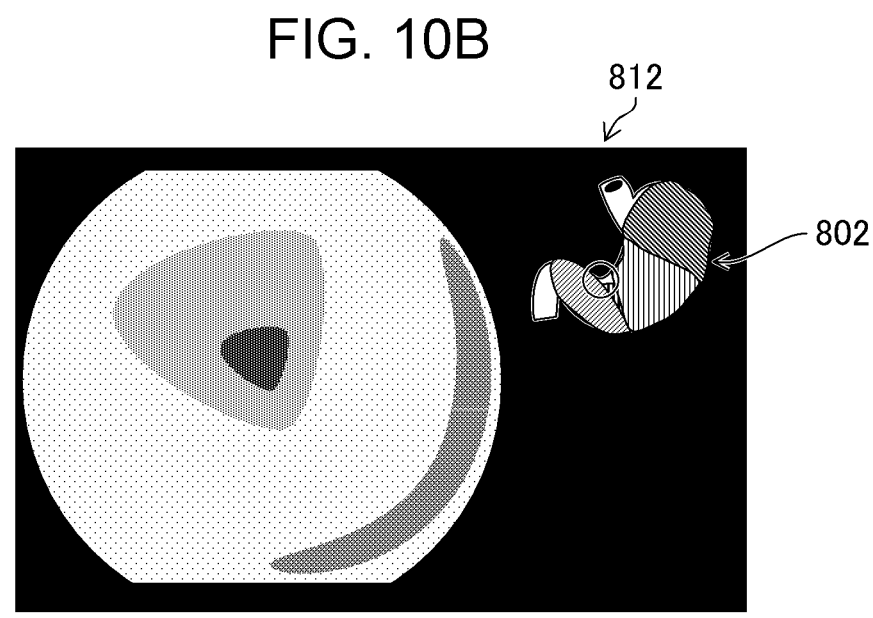

FIGS. 10A and 10B are diagrams illustrating a display example on the monitor 400 (a display). FIG. 10A illustrates a state during normal observation (a state in which an expected end timing has not come), and only an endoscopic image 810 (a normal observation image) is displayed. On the other hand, FIG. 10B illustrates a reporting state at an expected end timing, and an endoscopic image 812 is displayed such that the image 802 indicating an unobserved area (see FIG. 9B) is superimposed thereon. The reporting control unit 226 may display the image 802 on a screen different from that of the endoscopic image.

In the mode illustrated in FIG. 10B, the reporting control unit 226 causes the screen to newly display information (the image 802) that is not displayed on the screen before reporting is performed. Alternatively, the reporting control unit 226 may cause the speaker 209A to newly output a sound that is not output before reporting is performed, in addition to or instead of performing the screen display. In a case where there is a not-yet-imaged area, for example, the reporting control unit 226 is capable of performing reporting by outputting a warning sound, such as a beep, or a sound indicating a not-yet-imaged area, such as "the lesser-curvature-side-portion of angulus has not been imaged" at the time of reporting.

In the endoscope system 10, the user is able to operate the endoscope 100 in accordance with such a report indicating that imaging has not been performed (insufficient observation) and image (observe) a not-yet-imaged area. Thus, it is possible to prevent insufficient observation. In addition, in the endoscope system 10, reporting is performed at an appropriate timing (an expected end timing), and thus there is no possibility of disturbing observation.

If it is determined in step S140 that there is no not-yet-imaged area, the reporting control unit 226 preferably performs reporting in a mode different from the mode in which there is a not-yet-imaged area, for example, colors the entire schematic diagram in the same color, surrounds the entire schematic diagram with a circle (when a screen is displayed), or outputs a sound "there is no not-yet-imaged area". If there is no not-yet-imaged area, the reporting control unit 226 may make the reporting intensity lower than that in a case where there is a not-yet-imaged area (for example, reduce the size of the schematic diagram or reduce the volume of sound).

The CPU 210 and the image processing unit 204 repeat the process of steps S110 to S160 until observation ends (during NO in step S170).

Figure 11A:
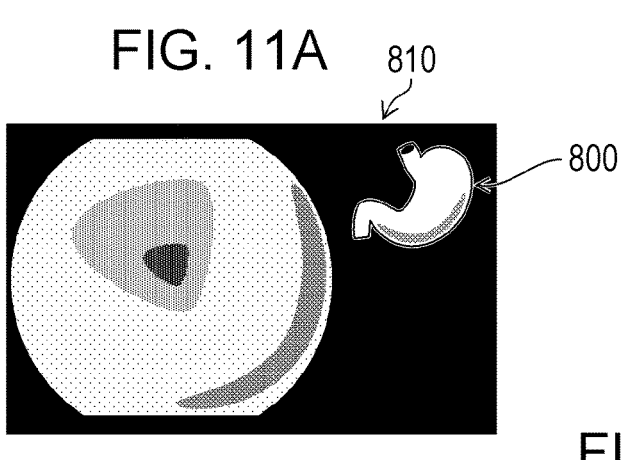
FIGS. 11A to 11D are still other diagrams illustrating an example of a method for reporting a determination result.
Figure 11B:
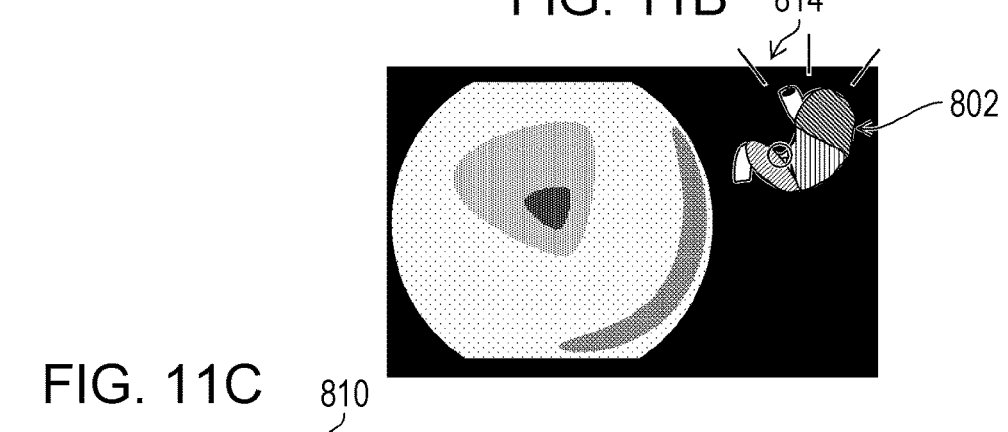

As described above, the medical image processing apparatus, the method for operating the medical image processing apparatus, and the endoscope system according to the present invention are capable of reporting insufficient observation at an appropriate timing.
Modification of Reporting Mode In the mode illustrated in FIGS. 10A and 10B, a schematic diagram of the stomach (the image 802) is not displayed in a superimposed manner during normal observation (screen display during normal observation is OFF; the radio button in the region 706 in FIG. 8 is OFF). However, as illustrated in FIG. 11A, a schematic diagram (for example, the image 800 illustrated in FIG. 9A) may be displayed in a superimposed manner also during normal observation (screen display during normal observation is ON). As illustrated in FIG. 11B, the reporting control unit 226 causes the image 802 to blink on the screen of the monitor 400 at the time of reporting (an expected end timing). The mode illustrated in FIGS. 11A to 11D is a mode of performing reporting by changing the display mode of information (the image 800) that is already being displayed on the screen on the monitor 400 (a display).

The reporting control unit 226 may perform reporting by changing the output mode of a sound that is already being output from the speaker 209A, in addition to or instead of performing screen display of information. For example, the reporting control unit 226 is capable of increasing a reporting intensity by changing the details, volume, tone, pattern, or the like of a sound (message) at an expected end timing, relative to the sound output during normal observation.

Figure 11C:
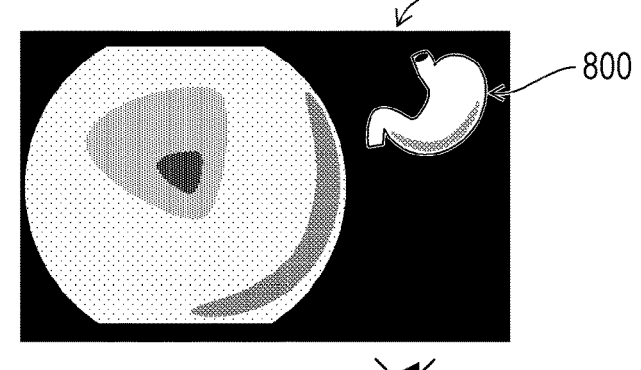
Figure 11D:
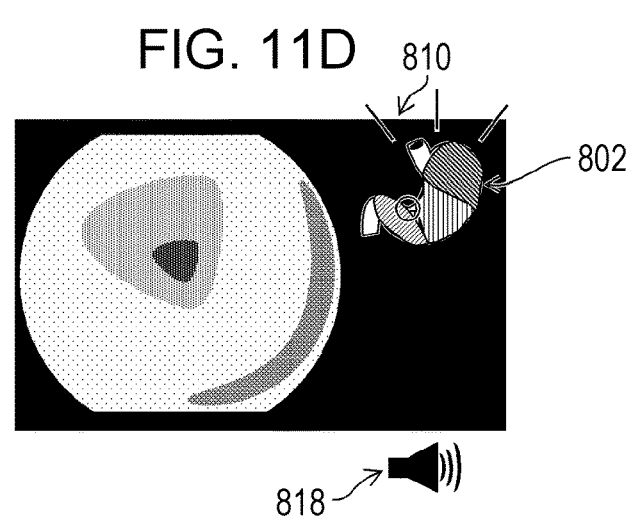
Figure 12:
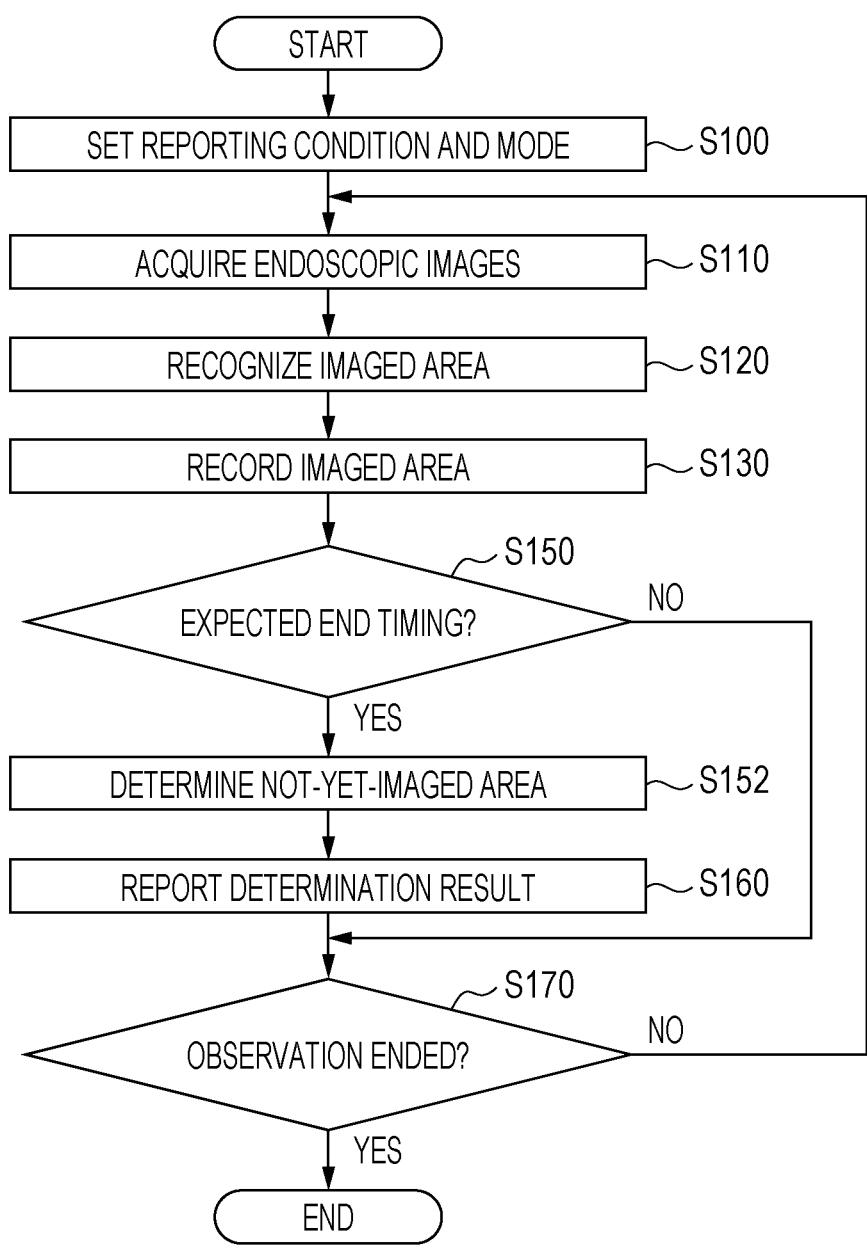
FIG. 12 is another flowchart illustrating a procedure of a medical image processing method according to the first embodiment.

FIG. 11C illustrates a state of normal observation (the image 800 is displayed; a cross is put on an icon 816 and no sound is output), and FIG. 11D illustrates a state of reporting (the image 802 blinks and a sound is output; an icon 818 is displayed).
Modification of Process Procedure In the mode illustrated in FIG. 7, a not-yet-imaged area is continuously determined at a timing other than an expected end timing. Alternatively, as illustrated in FIG. 12, the determining unit 224 may determine a not-yet-imaged area (step S152: a determination step) at an expected end timing (for example, a timing at which a user instruction is accepted, a timing at which an organ to be observed is changed, or a timing at which an image of a landmark is acquired). The flowchart in FIG. 12 is the same as that in FIG. 7 except step S152, and thus a description of the same part is omitted.

Figure 13:
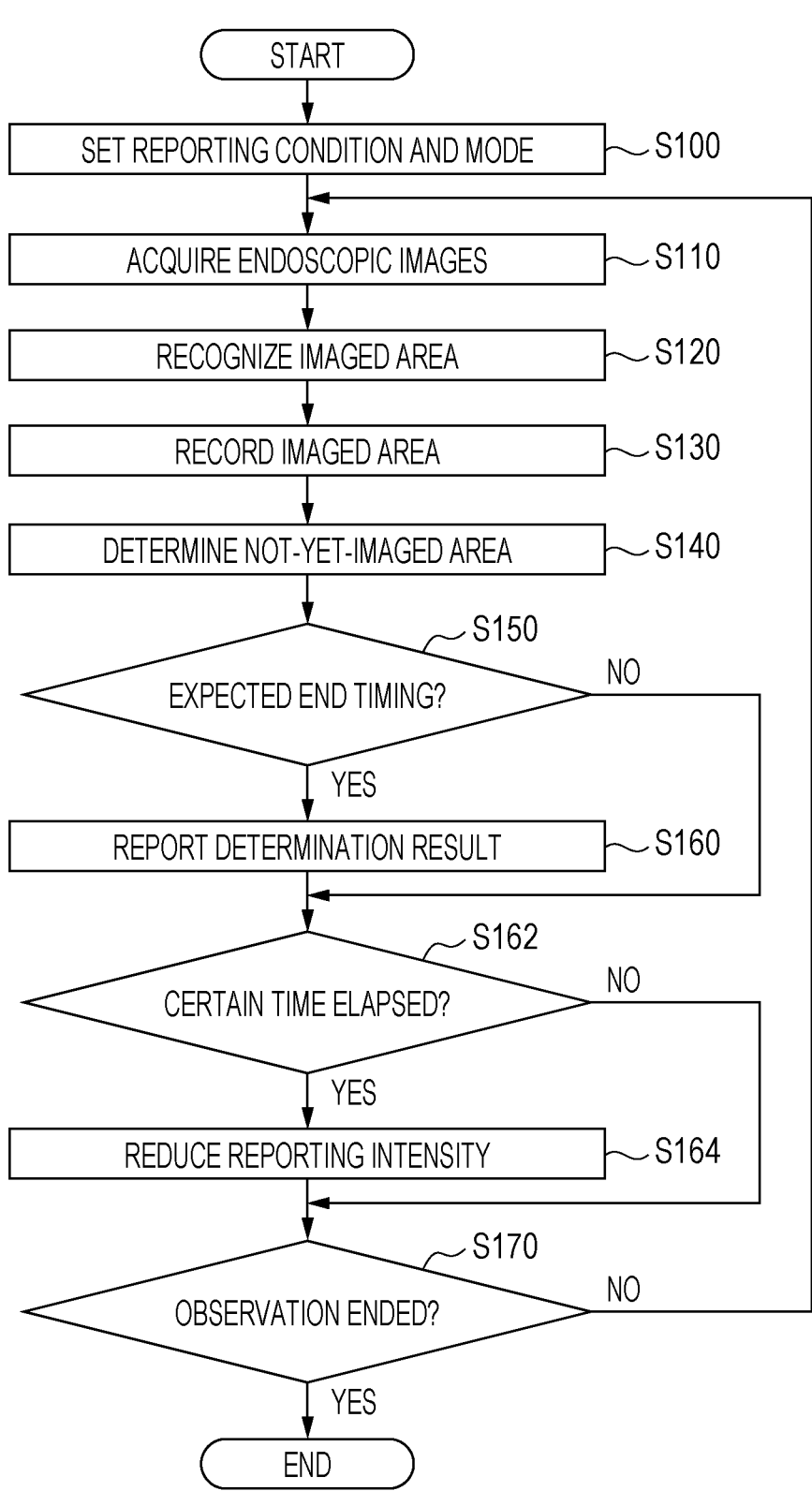
FIG. 13 is still another flowchart illustrating a procedure of a medical image processing method according to the first embodiment.

In consideration of "reporting does not disturb observation or diagnosis", the reporting control unit 226 may reduce the reporting intensity (including ending of reporting) after a certain time has elapsed from reporting, as illustrated in FIG. 13 (steps S162 and S164: a reporting step, see the region 716 in FIG. 8).
Modification of Area Recognition Method In the above-described first embodiment, a description has been given of a case where the area recognizing unit 222 performs area recognition by using a CNN. However, area recognition may use not only the CNN but also multi-class classification based on typical supervised learning, such as support vector machine (SVM) or k-nearest neighbor (k-NN).

APPENDICES

In addition to the above-described embodiment and modifications, the configurations described below are included in the scope of the present invention.

Appendix 1

A medical image processing apparatus wherein
a medical image analysis processing unit detects a region of interest on the basis of a feature quantity of pixels of a medical image, the region of interest being a region to be focused on, and
a medical image analysis result acquiring unit acquires an analysis result of the medical image analysis processing unit.

Appendix 2

A medical image processing apparatus wherein
a medical image analysis processing unit detects presence or absence of a target to be focused on, on the basis of a feature quantity of pixels of a medical image, and
a medical image analysis result acquiring unit acquires an analysis result of the medical image analysis processing unit.

Appendix 3

The medical image processing apparatus wherein
the medical image analysis result acquiring unit acquires the analysis result of the medical image from a recording device in which the analysis result is recorded, and the analysis result is either or both of the region of interest which is a region to be focused on included in the medical image and the presence or absence of the target to be focused on.

Appendix 4

The medical image processing apparatus wherein the medical image is a normal-light image acquired by radiating light in a white range or light in a plurality of wavelength ranges as the light in the white range.

Appendix 5

The medical image processing apparatus wherein
the medical image is an image acquired by radiating light in a specific wavelength range, and
the specific wavelength range is a range narrower than a white wavelength range.

Appendix 6

The medical image processing apparatus wherein the specific wavelength range is a blue or green range in a visible range.

Appendix 7

The medical image processing apparatus wherein the specific wavelength range includes a wavelength range of 390 nm or more and 450 nm or less or a wavelength range of 530 nm or more and 550 nm or less, and the light in the specific wavelength range has a peak wavelength in the wavelength range of 390 nm or more and 450 nm or less or the wavelength range of 530 nm or more and 550 nm or less.

Appendix 8

The medical image processing apparatus wherein the specific wavelength range is a red range in a visible range.

Appendix 9

The medical image processing apparatus wherein the specific wavelength range includes a wavelength range of 585 nm or more and 615 nm or less or a wavelength range of 610 nm or more and 730 nm or less, and the light in the specific wavelength range has a peak wavelength in the wavelength range of 585 nm or more and 615 nm or less or the wavelength range of 610 nm or more and 730 nm or less.

Appendix 10

The medical image processing apparatus wherein the specific wavelength range includes a wavelength range in which a light absorption coefficient is different between oxyhemoglobin and deoxyhemoglobin, and the light in the specific wavelength range has a peak wavelength in the wavelength range in which the light absorption coefficient is different between oxyhemoglobin and deoxyhemoglobin.

Appendix 11

The medical image processing apparatus wherein the specific wavelength range includes a wavelength range of 400±10 nm, a wavelength range of 440±10 nm, a wavelength range of 470±10 nm, or a wavelength range of 600 nm or more and 750 nm or less, and the light in the specific wavelength range has a peak wavelength in the wavelength range of 400±10 nm, the wavelength range of 440±10 nm, the wavelength range of 470±10 nm, or the wavelength range of 600 nm or more and 750 nm or less.

Appendix 12

The medical image processing apparatus wherein
the medical image is an inside-of-living-body image depicting an inside of a living body, and
the inside-of-living-body image has information about fluorescence emitted by a fluorescent substance in the living body.

Appendix 13

The medical image processing apparatus wherein the fluorescence is acquired by irradiating the inside of the living body with excitation light whose peak is 390 nm or more and 470 nm or less.

Appendix 14

The medical image processing apparatus wherein
the medical image is an inside-of-living-body image depicting an inside of a living body, and
the specific wavelength range is a wavelength range of infrared light.

Appendix 15

The medical image processing apparatus wherein the specific wavelength range includes a wavelength range of 790 nm or more and 820 nm or less or a wavelength range of 905 nm or more and 970 nm or less, and the light in the specific wavelength range has a peak wavelength in the wavelength range of 790 nm or more and 820 nm or less or the wavelength range of 905 nm or more and 970 nm or less.

Appendix 16

The medical image processing apparatus wherein
a medical image acquiring unit includes a special-light image acquiring unit that acquires a special-light image having information about the specific wavelength range on the basis of a normal-light image that is acquired by radiating light in a white range or light in a plurality of wavelength ranges as the light in the white range, and
the medical image is the special-light image.

Appendix 17

The medical image processing apparatus wherein a signal in the specific wavelength range is acquired through computation based on color information of RGB or CMY included in the normal-light image.

Appendix 18

The medical image processing apparatus including
a feature quantity image generating unit that generates a feature quantity image through computation based on at least one of a normal-light image or a special-light image, the normal-light image being acquired by radiating light in a white range or light in a plurality of
wavelength ranges as the light in the white range, the
special-light image being acquired by radiating light in
a specific wavelength range, wherein
the medical image is the feature quantity image.

Appendix 19

An endoscope apparatus including:
the medical image processing apparatus according to any
one of appendices 1 to 18; and
an endoscope that acquires an image by radiating at least
any one of light in a white wavelength range or light in
a specific wavelength range.

Appendix 20

A diagnosis assistance apparatus including the medical
image processing apparatus according to any one of appen-
dices 1 to 18.

Appendix 21

A medical work assistance apparatus including the medi-
cal image processing apparatus according to any one of appendices 1 to 18.
The embodiment of the present invention and other
examples have been described above. The present invention
is not limited to the above-described aspects and various
modifications can be made without deviating from the spirit
of the present invention.

REFERENCE SIGNS LIST 10 endoscope system 100 endoscope
102 handheld operation section
104 insertion section
106 universal cable
108 light guide connector
112 soft part
114 bending part
116 tip rigid part
116A distal-end-side surface
123 illumination unit
123A illumination lens
123B illumination lens
126 forceps port
130 imaging optical system
132 imaging lens
134 imaging element
136 driving circuit
138 AFE
141 air/water supply button
142 suction button
143 function button
144 imaging button
170 light guide
200 processor
202 image input controller
204 image processing unit
205 communication control unit
206 video output unit
207 recording unit
208 operation unit
209 audio processing unit
209A speaker 210 CPU
211 ROM
212 RAM
220 medical image acquiring unit
222 area recognizing unit
224 determining unit
226 reporting control unit
227 operation accepting unit
228 movement direction estimating unit
229 recording control unit
230 display control unit
232A input layer
232B intermediate layer
232C output layer
234 convolutional layer
235 pooling layer
236 fully connected layer
260 endoscopic image
262 area information
264 area recognition result
266 determination result
300 light source apparatus
310 light source
310B blue light source
310G green light source
310R red light source
310V violet light source
330 diaphragm
340 condenser lens
350 light source control unit
400 monitor
700 screen
702 region
704 region
706 region
708 region
710 region
712 region
714 region
716 region
800 image
802 image
804 circle
810 endoscopic image
812 endoscopic image
816 icon
818 icon
$F_1$ filter
$F_2$ filter
S100-S170 individual steps of a method for operating a
medical image processing apparatus
What is claimed is:
1. A medical image processing apparatus comprising:
a memory that stores area information indicating a plu-
rality of areas to be imaged in a photographic subject,
in advance; and
a processor, wherein
the processor is configured to
acquire a medical image of the photographic subject,
perform image recognition on the medical image using a
trained model,
in a case where at least one of following conditions (a),
(b), or (c):
(a) a specific subject continuously appears in the medi-
cal image for more than a predetermined time,
(b) a specific subject appears in a predetermined area of
the medical image, (c) a specific subject appears in the medical image at a size equal to or larger than a predetermined size is met, recognize an area of the subject in the medical image as an imaged area based on result of the image recognition, record information of the imaged area on a memory, compare the information of the imaged area with the area information indicating the plurality of areas to be imaged, and control to output information discriminating between the information of the imaged area and information indicating a not-yet-imaged area at an expected end timing that is automatically determined by the processor based on a change in an organ to be observed or a detection of a predetermined anatomical landmark in the medical image.

2. The medical image processing apparatus according to claim 1, wherein the processor is configured to store information of an area which is recognized as the imaged area on the memory, in association with the medical image.

3. The medical image processing apparatus according to claim 1, wherein the processor is configured to cause a display to display the information indicating the imaged area, together with the information indicating the not-yet-imaged area.

4. The medical image processing apparatus according to claim 1, wherein the processor is configured to cause the information indicating the imaged area and the information indicating the not-yet-imaged area to be displayed on a display screen the same as the medical image, using a schematic diagram.

5. The medical image processing apparatus according to claim 4, wherein the processor is configured to cause the information indicating the imaged area and the information indicating the not-yet-imaged area, to be displayed with a display mode different from each other in the schematic diagram.

6. The medical image processing apparatus according to claim 1, wherein the processer is configured to perform the image recognition using a neural network.

7. The medical image processing apparatus according to claim 1, wherein the predetermined area is an esophagogastric junction.

8. The medical image processing apparatus according to claim 1, wherein the predetermined area is a pharynx.

9. The medical image processing apparatus according to claim 1, wherein the processor is configured to make the determination at a timing at which the medical image of the predetermined area is acquired.

10. The medical image processing apparatus according to claim 1, wherein the processor is configured to reduce an intensity of the output, upon elapse of a predesignated time after starting the outputting.

11. The medical image processing apparatus according to claim 1, wherein the processor is configured to cause a display which displays of information in a screen and/or a speaker which outputs a sound, to perform the outputting.

12. The medical image processing apparatus according to claim 11, wherein the processor is configured to control to output by changing a display mode of the information that is already being displayed in the screen on the display and/or an output mode of the sound that is already being output from the speaker.

13. The medical image processing apparatus according to claim 11, wherein, in controlling the outputting, the processor causes the display to newly perform display of information that is not displayed in the screen before the outputting is performed, and/or causes the speaker to newly output a sound that is not output before the outputting starts.

14. The medical image processing apparatus according to claim 11, wherein the processor is configured to increase or decrease an intensity of display in the screen by the display.

15. An endoscope system comprising:

the medical image processing apparatus according to claim 1; and an endoscope configured to be inserted into a subject as the photographic subject and capture the medical image, wherein the processor is configured to acquire the medical image captured by the endoscope.

16. The endoscope system according to claim 15, wherein the processor is configured to estimate a movement direction of the endoscope, and cause a result of the determination to be output at a timing when the estimated movement direction is changed to a backward direction or later.

17. A method for operating a medical image processing apparatus comprising a memory that stores area information indicating a plurality of predetermined areas to be imaged in a photographic subject, and a processor, the method comprising:

acquiring a medical image of the photographic subject;

performing image recognition on the medical image using a trained model;

in a case where at least one of following conditions (a), (b), or (c):

(a) a specific subject continuously appears in the medical image for more than a predetermined time, (b) a specific subject appears in a predetermined area of the medical image, (c) a specific subject appears in the medical image at a size equal to or larger than a predetermined size is met, recognizing an area of the subject in the medical image as an imaged area based on result of the image recognition;

recording information of the imaged area on a memory;

comparing the information of the imaged area with the area information indicating the plurality of areas to be imaged; and controlling to output information discriminating between the information of the imaged area and information indicating a not-yet-imaged area at an expected end timing that is automatically determined by the processor based on a change in an organ to be observed or a detection of a predetermined anatomical landmark in the medical image.

18. The method for operating a medical image processing apparatus according to claim 17, wherein the image recognition is performed using a neural network.

* * * * *